United States Patent [19]

Eggers

[11] Patent Number: 5,480,398
[45] Date of Patent: Jan. 2, 1996

[54] ENDOSCOPIC INSTRUMENT WITH DISPOSABLE AUTO-REGULATING HEATER

[75] Inventor: Philip E. Eggers, Dublin, Ohio

[73] Assignee: Hemostatic Surgery Corporation, Georgetown, Cayman Islands

[21] Appl. No.: 245,304

[22] Filed: May 17, 1994

Related U.S. Application Data

[63] Continuation of Ser. No. 960,471, Oct. 9, 1992, abandoned, which is a continuation-in-part of Ser. No. 877,476, May 1, 1992, abandoned.

[51] Int. Cl.⁶ ..................................................... A61B 17/32
[52] U.S. Cl. ................................ 606/29; 606/28; 606/39; 606/46
[58] Field of Search .......................... 606/28–34, 37–42, 606/45–52; 219/10.75

[56] References Cited

U.S. PATENT DOCUMENTS

| | | |
|---|---|---|
| Re. 33,644 | 7/1991 | Hall ................................. 219/10.75 X |
| 1,975,436 | 10/1934 | Sorrel et al. . |
| 2,181,274 | 11/1939 | Jackson et al. . |
| 2,947,841 | 8/1960 | Pickles et al. . |
| 2,951,927 | 9/1960 | Weller . |
| 3,218,384 | 11/1965 | Shaw . |
| 3,296,364 | 1/1967 | Mason . |
| 3,316,344 | 4/1967 | Kidd et al. . |
| 3,489,884 | 1/1970 | Waseleski, Jr. . |
| 3,515,837 | 6/1970 | Ando . |
| 3,524,966 | 8/1970 | Ando . |
| 3,584,190 | 6/1971 | Marcoux . |
| 3,662,152 | 5/1972 | Weller et al. ................... 219/10.75 X |
| 3,768,482 | 10/1973 | Shaw . |
| 3,826,263 | 7/1974 | Cage et al. . |
| 3,975,819 | 8/1976 | Ando . |
| 3,987,795 | 10/1976 | Morrison ................................. 606/48 |
| 4,079,192 | 3/1978 | Josse . |
| 4,091,813 | 5/1978 | Shaw et al. . |
| 4,185,632 | 1/1980 | Shaw ................................. 606/45 |
| 4,207,896 | 6/1980 | Shaw . |
| 4,256,945 | 3/1981 | Carter et al. . |
| 4,456,186 | 6/1984 | Ando . |
| 4,481,057 | 11/1984 | Beard . |
| 4,485,810 | 12/1984 | Beard . |
| 4,615,330 | 10/1986 | Nagasaki et al. ................... 606/46 X |
| 4,615,330 | 10/1986 | Nagasaki et al. . |
| 4,626,767 | 12/1986 | Clappier et al. . |
| 4,640,279 | 2/1987 | Beard . |
| 4,701,587 | 10/1987 | Carter et al. . |
| 4,745,264 | 5/1988 | Carter . |

(List continued on next page.)

FOREIGN PATENT DOCUMENTS

| | | |
|---|---|---|
| 0107927 | 5/1984 | European Pat. Off. . |
| 0110692 | 6/1984 | European Pat. Off. . |
| 0130671 | 1/1985 | European Pat. Off. . |
| 0209215 | 1/1987 | European Pat. Off. . |
| 41-2676 | 2/1966 | Japan . |
| 41-1743 | 2/1966 | Japan . |
| 43-18838 | 8/1968 | Japan . |
| 49-5699 | 2/1974 | Japan . |
| 50-84373 | 7/1975 | Japan . |
| 54-57242 | 5/1979 | Japan . |
| 1076772 | 7/1967 | United Kingdom . |

OTHER PUBLICATIONS

Tudbury, C. A., "Skin Effect and Proximity Effect," Sixth Biennial IEEE Conference on Electric Heating, pp. 78–88, Apr. 1963.

Primary Examiner—Stephen C. Pellegrino
Assistant Examiner—Michael Peffley
Attorney, Agent, or Firm—Fish & Neave; Nicola A. Pisano

[57] ABSTRACT

An instrument for use in endoscopic surgery is provided. The instrument has a reusable shaft to which a disposable working tip can be removably attached. The disposable working tip has a working surface for providing hemostasis at an auto-regulated temperature. The working surface may include a tapered edge for providing thermally-enhanced cutting and a non-stick coating for operating the instrument at low auto-regulation temperatures. The instrument is capable of being used for a wide variety of endoscopic surgical procedures.

40 Claims, 15 Drawing Sheets

U.S. PATENT DOCUMENTS

| | | |
|---|---|---|
| 4,770,067 | 9/1988 | Liu et al. . |
| 4,802,476 | 2/1989 | Noerenberg et al. . |
| 4,839,501 | 6/1989 | Cowell . |
| 4,848,337 | 7/1989 | Shaw et al. ............... 606/45 |
| 4,869,248 | 9/1989 | Narula ............... 606/45 |
| 4,936,842 | 6/1990 | D'Amelio et al. ............... 606/48 |
| 5,013,312 | 5/1991 | Parins et al. . |
| 5,047,025 | 9/1991 | Taylor et al. . |
| 5,071,419 | 12/1991 | Rydell et al. ............... 606/48 |
| 5,078,256 | 2/1992 | Taylor et al. . |
| 5,080,660 | 1/1992 | Buelna ............... 606/46 X |
| 5,089,002 | 2/1992 | Kirwan, Jr. ............... 606/45 |
| 5,197,963 | 3/1993 | Parins ............... 606/48 |
| 5,223,689 | 6/1993 | Cowell et al. ............... 219/10.75 X |

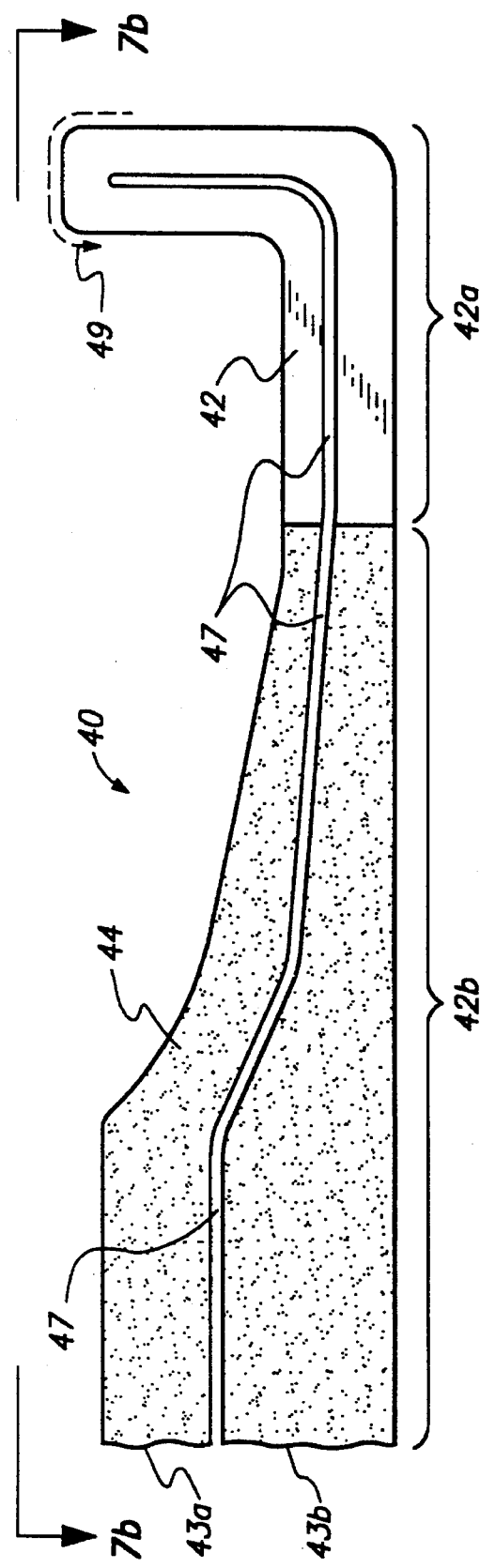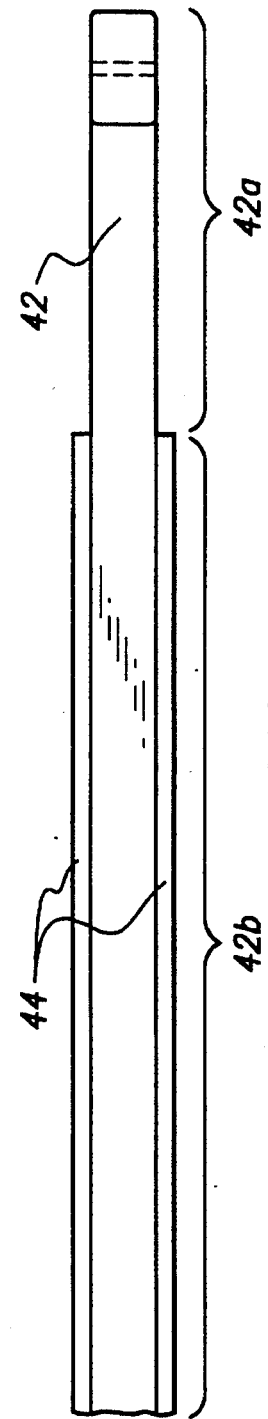
FIG 7a
FIG. 7b

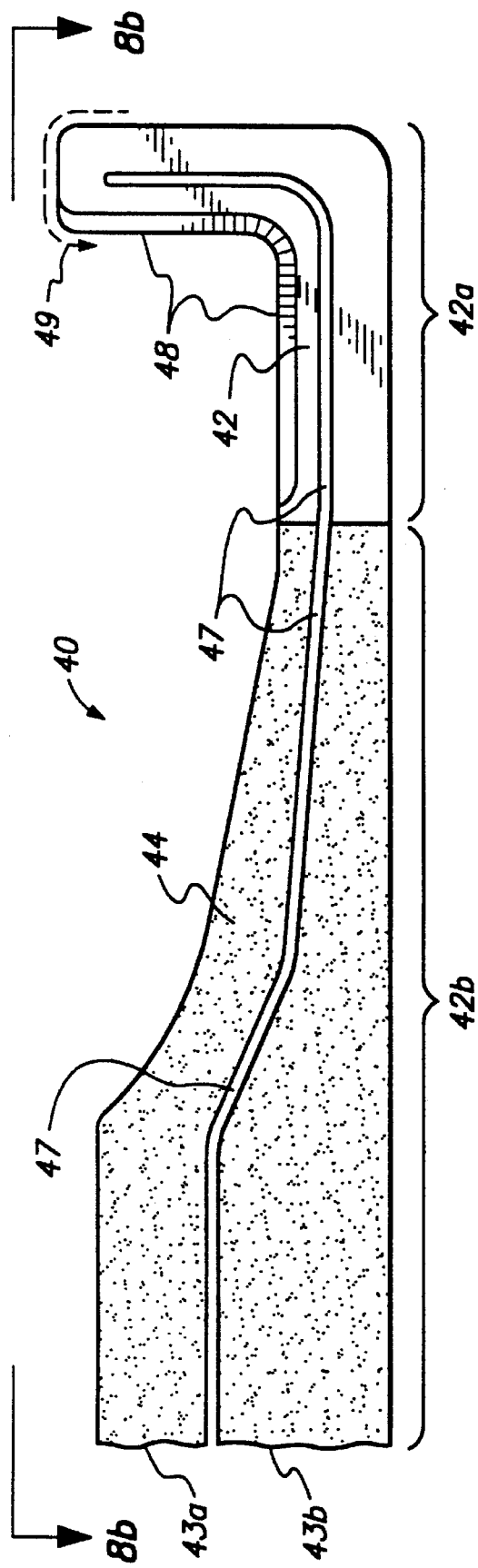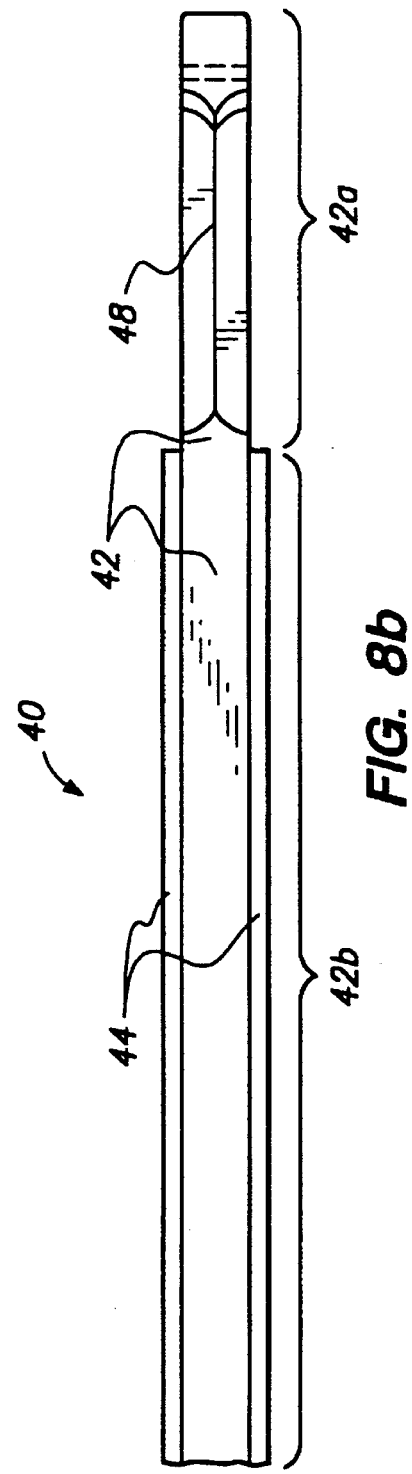

ENDOSCOPIC INSTRUMENT WITH DISPOSABLE AUTO-REGULATING HEATER

CROSS REFERENCE TO RELATED APPLICATION

This is a continuation, of application Ser. No. 07/960,471, filed Oct. 9, 1992, now abandoned, entitled ENDOSCOPIC INSTRUMENT WITH DISPOSABLE AUTO-REGULATING HEATER, which is a continuation-in-part of application Ser. No. 07/877,476, filed May 1, 1992, now abandoned.

BACKGROUND OF THE INVENTION

This invention relates to instruments for use in endoscopic surgery. More particularly, this invention relates to instruments with a disposable auto-regulating heater for use in endoscopic surgery.

Minimally invasive surgery such as endoscopic surgery allows for major surgical operations to be performed with reduced pain and disability relative to conventional "open" surgery. In performing endoscopic surgery, the surgeon does not cut a large incision through the body wall to obtain access to the tissue requiring treatment. Instead, an endoscope, typically a miniaturized video camera, and certain specially-designed surgical instruments are inserted through a trocar tube or similar device. Trocar tubes, typically having a 5 mm to 10 mm inside diameter, produce only a small opening. The image provided by the endoscope is displayed on a large video screen or other type of monitor, thereby affording the surgeon enhanced visual control of the specially-designed instruments.

Endoscopic surgery is possible whenever a small optical instrument (endoscope) and miniaturized operating instruments can be inserted into the body cavity or other anatomical space. Such miniaturized operating instruments have been developed for endoscopic surgery in the abdomen ("laparoscopy"), in the chest ("thoracoscopy") and in joints ("arthroscopy").

In performing both "open" and endoscopic surgical procedures, the surgeon must control bleeding that occurs when tissues are incised. Such bleeding obscures the surgeon's vision, reduces precision, and often necessitates slow and elaborate procedures to perform the surgery.

Controlling flow of blood from incised tissue is readily accomplished in "open" surgical procedures, because the surgeon can directly touch and manipulate the various tissues. Bleeding from incised tissue is controlled by blotting or evacuating the accumulating blood. This step of removing the blood permits visual observation of the vessels for clamping or tying of those vessels to inhibit further blood loss.

In performing endoscopic surgery, the surgeon forgoes direct manual access to the tissue being operated upon. Thus, traditional means of physically controlling bleeding (i.e., clamping and tying) are unavailable. Other techniques must then be employed to control bleeding during the surgical procedure. One such technique, which was first employed in "open" surgical procedures, is to thermally heat the bleeding tissue. Such thermal heating reduces the tendency of severed tissue to bleed.

For "open surgery" it is known to provide surgical scalpels which employ a blade with an adjacent resistive heating element. The resistive heating element provides thermally-enhanced cutting, in addition to hemostasis, when electrical current is passed through the element. Although such resistive elements can be readily brought to a suitably high and constant temperature in air prior to contacting tissue, they rapidly cool when brought into contact with tissue. During "open" surgery, non-predictable and continually varying portions of the blade contact the tissue as it is being cut. As the blade cools, its ability to cut tissue and provide hemostasis becomes markedly less effective. Furthermore, tissue tends to adhere to the blade. If additional power is applied by conventional means to counteract this cooling, the additional power may be delivered to the uncooled portions of the blade, thus resulting in tissue damage and blade destruction.

Shaw U.S. Pat. No. 4,185,632 shows an improved surgical cutting instrument in which the temperature of the cutting portion of the blade is self-regulating. Radio frequency electrical currents maintain the temperature within an elevated preselected temperature range. These currents flow within variable skin depths in an electrical conductor disposed near the cutting edge of the blade. This variable skin depth effect produces self-regulation of the blade temperature.

In addition to the ability to provide hemostasis, and to remotely cut and dissect tissue, endoscopic surgery requires the use of instruments that reduce adherence of tissue to the instrument. Coagulum buildup and sticking limits the usefulness of the instrument and may cause undesirable tissue damage and bleeding. Also, the adherence of tissue to such surgical instruments limits the surgeon's control of the instrument.

It would therefore be desirable to provide a low cost hemostatic instrument for endoscopic surgery which has the ability to precisely control the location and quantity of thermal energy which is delivered to tissue.

It would also be desirable to provide an endoscopic instrument that has the ability to provide localized and precise thermally-enhanced cutting of tissue.

It would further be desirable to provide an endoscopic instrument which reduces the adherence of tissue and coagulum to the instrument so as to reduce tissue damage associated with such adherence and to maintain good thermal power delivery between the heating means and the tissue by reducing the thermal impedance associated with tissue or coagulum build up on said heating means.

In addition to the above, it would still further be desirable to provide an endoscopic instrument that is capable of being used for a wide variety of endoscopic surgical procedures. Thus, it would also desirable to provide an endoscopic instrument that has a reusable universal handle which is capable of accommodating a wide variety of disposable working surfaces wherein a used working surface can be easily removed from the handle and replaced with a new or differently shaped working surface.

SUMMARY OF THE INVENTION

In view of the foregoing, it is an object of this invention to provide a low cost hemostatic instrument for endoscopic surgery which has the ability to precisely control the location and quantity of thermal energy that is delivered to operative tissue.

It is another object of this invention to provide an endoscopic instrument that has the ability to provide localized and precise thermally-enhanced cutting of tissue.

It is a further object of this invention to provide an endoscopic instrument which reduces the adherence of tissue and coagulum to the instrument so as to reduce tissue damage associated with such adherence and to maintain good thermal power delivery between the heating means and the tissue by reducing the thermal impedance associated with tissue or coagulum build up on said heating means.

It is a still further object of this invention to provide an endoscopic instrument that is capable of being used for a variety of endoscopic surgical procedures. Thus, it is an object of this invention to provide an endoscopic instrument that has a reusable universal handle which is capable of accommodating a wide variety of disposable working surfaces wherein a used working surface can be easily removed from the handle and replaced with a new or different one.

In accordance with the present invention there is provided a disposable working tip for use in endoscopic surgery. The disposable working tip is adapted to be disposed from an end of a reusable elongated shaft and includes: a disposable heating element having first and second electrodes adapted to be removably attached to the end of the reusable elongated shaft and having a working surface for contacting tissue, wherein the working surface is maintained at an auto-regulated temperature, the heating element comprising a material having a skin depth responsive to the temperature of the heating element and that decreases as the temperature of the element falls below the auto-regulated temperature.

The working surface of the disposable heating element may also include an optional tapered edge for thermally-enhanced cutting of tissue and an electrically insulating non-stick coating to reduce coagulum buildup.

The above disposable working tip may also include an end cap having a passageway therethrough adapted to permanently hold the disposable heating element; and an engagement means disposed on the end cap for removably attaching the disposable working tip to the end of the reusable elongated shaft.

In accordance with the present invention, there is also provided an instrument for use in endoscopic surgery comprising the above disposable working tip in conjunction with a reusable elongated shaft having a proximal end and a distal end, the proximal end of the shaft having a pair of electrical terminals adapted to be coupled to a power supply.

BRIEF DESCRIPTION OF THE DRAWINGS

The above and other objects and advantages of the present invention will be apparent upon consideration of the following detailed description, taken in conjunction with accompanying drawings, in which like reference characters refer to like parts throughout, and in which:

FIGS. 7A and 7B are, respectively, plan and elevation views of an alternative embodiment of the present invention incorporating a monolithic heating element;

FIGS. 8A and 8B are, respectively, plan and elevation views of an endoscopic instrument constructed as shown in of FIGS. 7A and 7B, further incorporating the optional tapered thermally-enhanced cutting edge of the present invention;

DETAILED DESCRIPTION OF THE INVENTION

Figure 1:
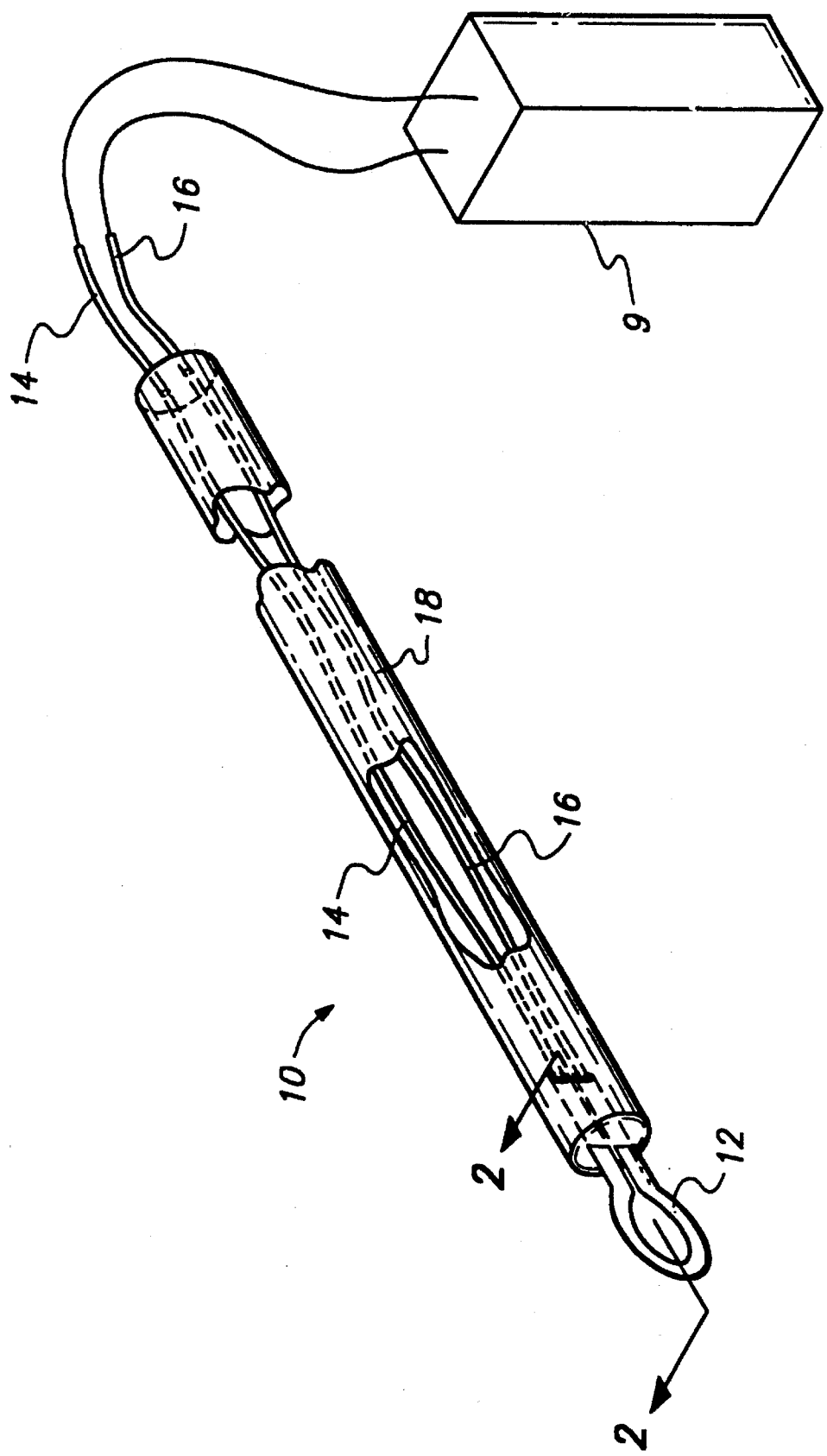
FIG. 1 is a perspective view, partly in section, of endoscopic surgical apparatus constructed in accordance with the principles of the present invention.
Figure 2:
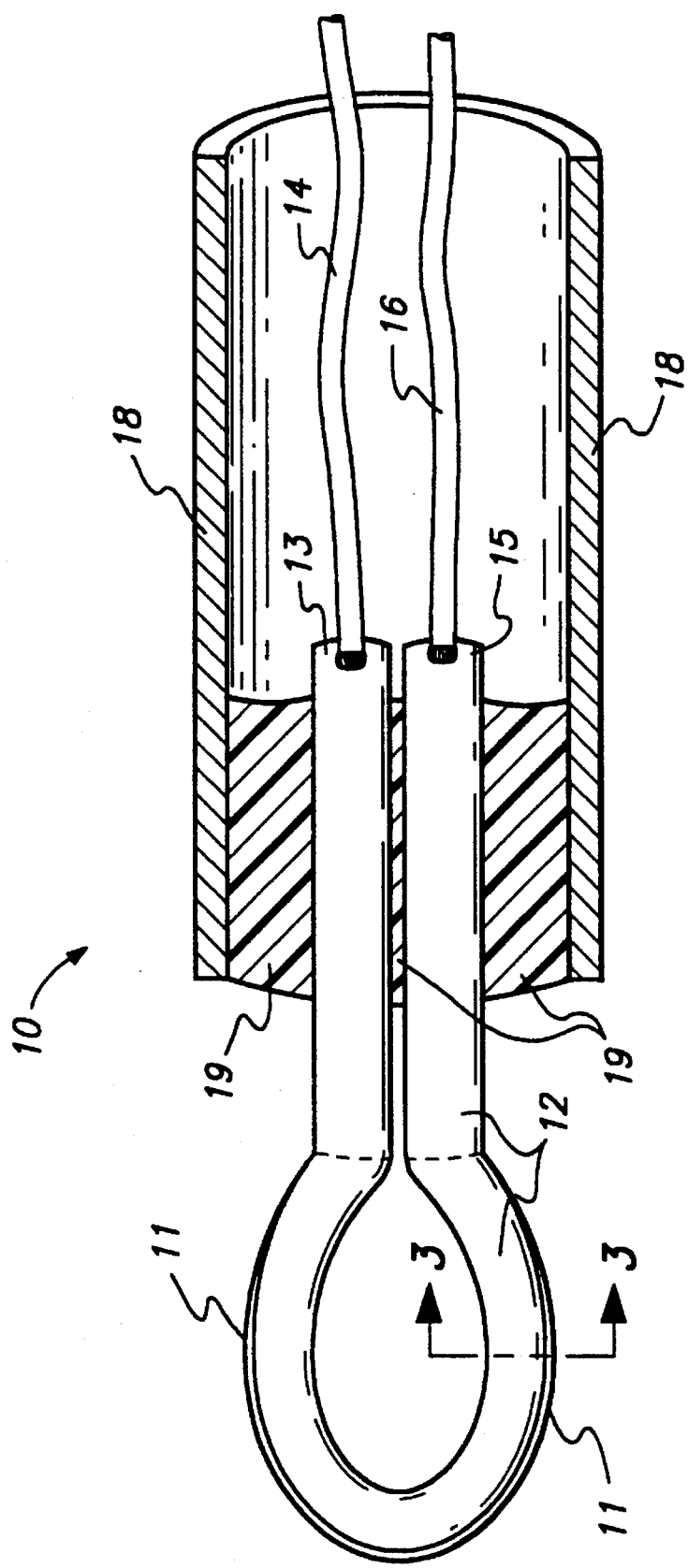
FIG. 2 is a cross-sectional view of the endoscopic instrument of FIG. 1, taken along line 2—2 of FIG. 1.

Referring to FIGS. 1 and 2, an illustrative embodiment of endoscopic instrument 10 of the present invention is described. The working surface of this instrument may be used for causing hemostasis of incised tissue or for directly coagulating small tissue masses, either with or without simultaneously incising the tissue. Endoscopic instrument 10 includes an elongated shaft 18 having proximal and distal ends. Elongated shaft 18 may be either flexible or rigid, depending upon the intended application. A working end comprising heating element 12 is disposed from the distal end of elongated shaft 18, while a handle (not shown) for facilitating manipulation of the instrument is disposed from the proximal end of elongated shaft 18. Electrical leads 14 and 16 extend both to the handle, where they are then connected to power source 9, and to heating element 12 on the distal end of elongated shaft 18.

Endoscopic instrument 10 works as follows. Power source 9 provides an alternating current (AC) electrical potential to terminals 13 and 15, respectively, of heating element 12 through electrical leads 14 and 16. In response the imposed electrical potential, an electrical current is conducted through heating element 12. That current results in joulean heating, which raises the temperature of heating element 12 above body temperature (i.e., approximately 37° C.) to facilitate hemostasis and optionally permit thermally-enhanced cutting of tissue.

The present invention provides auto-regulation of the temperature of heating element 12. This self-regulating temperature feature results from constructing heating element 12 of a ferromagnetic material, or other material which undergoes a similar transition in current conduction properties when the temperature of the material varies. It is known that in such materials an AC current is confined to a region adjacent the surface of the material. This phenomena is commonly called the "skin effect." The current density is generally greatest at the surface and decreases in magnitude further into the material where the electric field approaches zero. The depth at which the skin effect current is reduced to about 37 percent of its surface value is referred to as the "skin depth" and is a function of the electrical resistivity, the magnetic permeability of the material conducting the current, and the frequency of the applied alternating electric potential. It is known that the skin depth $T_{SD}$, in centimeters, can be generally represented by the equation:

$$T_{SD}=(4\times10^3)sqrt(rho/[uf])$$

where rho is electrical resistivity in ohmcentimeters, u is relative magnetic permeability, and f is frequency in Hertz.

Ferromagnetic materials such as iron, nickel, cobalt, and their alloys, exhibit large changes in relative permeability as the temperature goes through a transition point called the "Curie" point. Because the relative permeability changes in response to the temperature of the material, the associated skin depth also changes, and therefore the amount of current conduction through the skin layer undergoes a transition near the Curie point. This transition in current conduction properties is used, as described hereinafter, to achieve auto-regulation of the temperature of heating element 12.

An auto-regulated endoscopic instrument is obtained in accordance with the present invention by causing a radio frequency (RF) current to flow in heating element 12. Heating element 12 may be composed of a ferromagnetic material or the like and uses the skin effect of the material to auto-regulate the temperature of the heating element. Heating element 12 is constructed of a material having it's current conduction transition at or near the auto-regulation temperature desired for the particular endoscopic surgical application. When heating element 12 is heated so that when a working surface of heating element 12 contacts tissue, that region of the heating element cools below the transition temperature. In response to the local temperature drop in the heating element, the associated skin depth responsively decreases as a result of the Curie transition in the heating element material. The reduced skin depth in turn results in an increase in local power dissipation, so that the temperature automatically tends to increase towards the auto-regulation temperature. Accordingly, the present invention uses the skin depth effect of the heating element material to maintain the working surface of the endoscopic instrument substantially at the auto-regulated temperature throughout the range of conditions encountered during surgery.

For example, for many iron-nickel alloys the Curie transition occurs at about 450° C., above which the relative permeability is near unity. Below about 450° C., the relative permeability is high, perhaps 100 to 1000, for the magnetic field strengths suitable for use in endoscopic surgical instruments. Thus, when the local temperature of a heating element constructed of this material falls below about 450° C., due to local cooling of the heating element when it comes into contact with cool tissue, the associated skin depth decreases more than 10 to 1. The decrease in skin depth results in an increase in local power dissipation and, thus, an increase in heating to provide auto-regulation of the heating element temperature.

In accordance with the present invention, heating element 12 may be composed of a ferromagnetic material or other material which undergoes a similar transition in current conduction properties, as the temperature of the material varies through the desired auto-regulation temperature, as discussed above. Preferably, heating element 12 is composed of an alloy of nickel and iron. Examples I and II, provide illustrative embodiments wherein the auto-regulation temperature is varied by varying the percentage of nickel and iron present in heating element 12.

Example I

For an auto-regulation temperature of approximately 315° C. at 1.8 megahertz, the alloy may be approximately 42% nickel and 58% iron. Such an alloy is available as LOW EXPANSION ALLOY 42, from Carpenter Technology Corporation of Reading, Pa., and has the following characteristics: unannealed, a hardness of approximately 91 Rockwell B, a tensile strength of approximately 98.5 ksi, an electrical resistivity at 23° C. of approximately 373 Ohms-cir mil/foot and a coefficient of thermal expansion of approximately 3.1 (IN/IN F×10-6) from approximately 77° to 700° F. Applicant has obtained satisfactory auto-regulation performance with devices constructed of this alloy wherein the working end of the heating element was approximately 18 mils (0.46 mm) thick with a thermostat cold finish.

Example II

For an auto-regulation temperature of approximately 550° C. at 1.8 megahertz, the alloy may be approximately 51% nickel and 49% iron. Such an alloy is available as GLASS SEAL 52, also from Carpenter Technology Corporation of Reading, Pa., and has the following characteristics: unannealed, and with a coefficient of thermal expansion of approximately 10.0 (IN/IN C×10-6) from approximately 25° to 550° C. Applicant has obtained satisfactory performance with devices constructed of this alloy wherein the working end of the heating element was approximately 20 mils (0.51 mm) thick.

After the heating element material has been selected, whether or not containing nickel or iron as in Examples I and II above, the heating element may then be configured into a variety of shapes, only one of which is shown in FIGS. 1 and 2. Of course, the particular shape desired depends upon the application of the particular endoscopic instrument.

In accordance with another feature of the present invention, it is desirable that the cross-sectional dimensions of heating element 12 be chosen to allow the electrical conductance of heating element 12 to change by at least a factor of 4 to 5 as the temperature of the working surface varies near the auto-regulation temperature. This feature of the present invention is illustrated by FIGS. 3A and 3B.

Figure 3A:
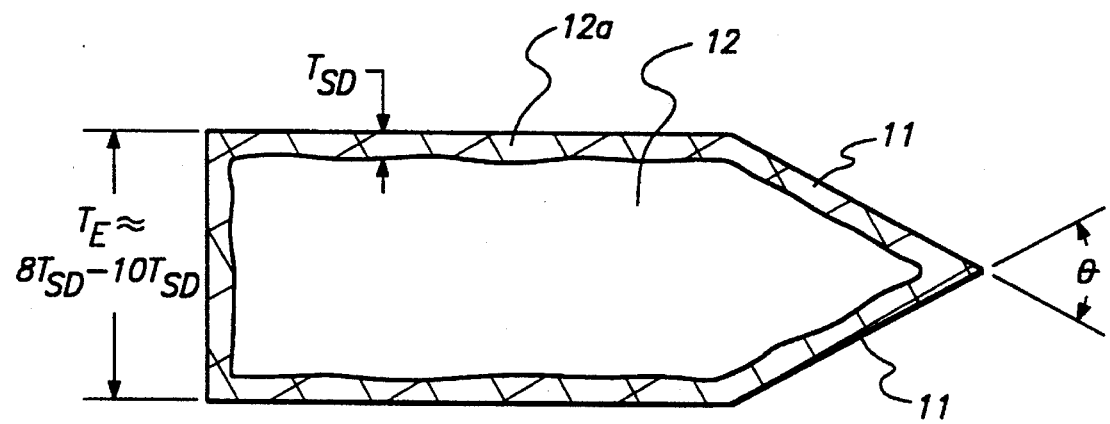
FIGS. 3A and 3B are illustrative cross-sectional views of heating element 12 of FIGS. 1 and 2, taken along line 3—3 of FIG. 2, at temperatures slightly below and above the auto-regulation temperature, respectively.
Figure 3B:
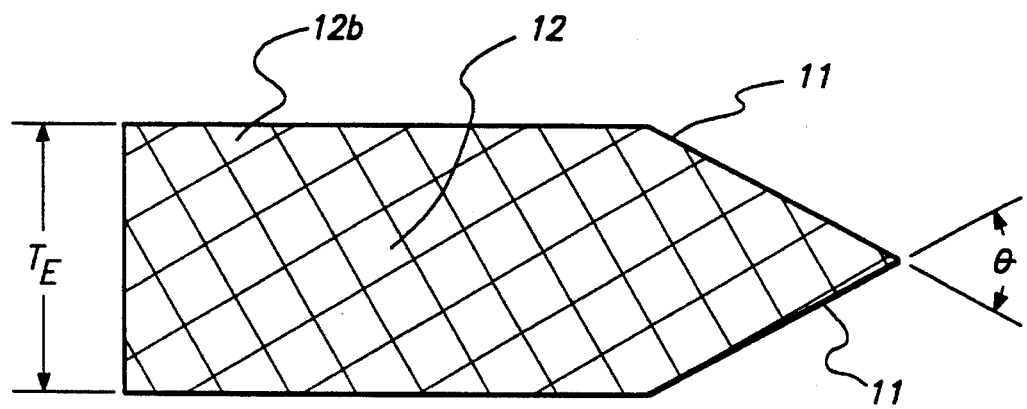

As shown in FIG. 3A, when the working surface temperature is slightly below the auto-regulation temperature, current 12a is confined to conduct in a region defined by the skin depth $T_{SD}$ of heating element 12. In accordance with the present invention, it is desirable that thickness $T_E$ of heating element 12 be approximately eight to ten times the skin depth $T_{SD}$, so that as the temperature of heating element 12 varies near the auto-regulation temperature, the electrical conductance of the element changes by a factor of about four to five. In FIG. 3B, where the heating element is at a working surface temperature slightly in excess of the auto-regulation temperature, electrical current 12b conducts throughout substantially the entire cross section of heating element 12 because the skin depth is then greater than half of the thickness $T_E$ of heating element 12. Thus, the effective electrical conductance of heating element 12 increases by a factor of four to five as it varies near the autoregulation temperature, as shown in FIGS. 3A and 3B.

After the shape and cross-sectional dimensions of heating element 12 are chosen, heating element 12 may be constructed using any method which produces geometrical dimensions that are consistent with the desired design tolerances of the working surface. For example, such methods include electric-discharge machining (EDM), blanking and chemical milling.

Heating element 12 is affixed to the distal end of elongated shaft 18 by potting material 19, which electrically isolates heating element 12 and electrical leads 14 and 16 from elongated shaft 18. Potting material 19 should, in addition, be suitable for use in the temperature range experienced by heating element 12. Furthermore, it is desirable that potting material 19 be able to withstand typical conditions encountered in steam-sterilization procedures and have a viscosity that would allow it to be placed into the inner portion of elongated shaft 18. Accordingly, the potting material may be comprised of plastic, ceramic, silicone or epoxy-based materials.

Elongated shaft 18 has a diameter compatible with minimally invasive surgery, for example, standard trocar tube inside diameters of 5 or 10 mm, and a length that allows a surgeon to perform an endoscopic procedure, for example, 13 inches. Preferably, elongated shaft 18 is made of a high thermal conductivity material so as to dissipate (i.e., distribute over the full length of said elongated shaft) that heat which conducts from heating element 12 located at the distal end of the shaft. This feature reduces the potential that non-targeted tissue will be subjected to high temperatures that might cause damage.

For example, elongated shaft 18 may be constructed of copper or the like and be plated with chrome on its outer surface. The chrome plating provides a cosmetic dull-mat finish to the copper, which would normally otherwise oxidize, and facilitates conventional steam-sterilization procedures.

An additional feature of the present invention is that a portion of elongated shaft 18 near the distal end may be flexible so as to permit insertion of the instrument within a patient's curved passageway. Alternatively, the flexible portion may extend to the proximal end so that the elongated shaft may be inserted into a circuitous passageway, for example, an intestinal tract. Such a shaft allows the working surface of instrument 10 to reach remote treatment sites, e.g., sites some distance beyond the entrance to the colon.

Electrical leads 14 and 16, which are connected to power source 9, should be capable of delivering the necessary AC current to heating element 12 with low electrical power loss. To avoid behavior associated with the skin effect, electrical leads 14 and 16 may each be composed of multiple strands of wire, wherein the individual strands are insulated from each other. The insulation allows AC current to flow through each individual strand but not between strands. A suitable wire is available as TYPE 2 LITZ WIRE (5×16×40), from Cooner Wire of Chatsworth, Calif. This particular wire is composed of 5 groups of 16 strands (i.e., a total of 80 strands), wherein each strand, which are insulated from each other, is of type 40 AWG.

In accordance with another feature of the present invention, when it is desired to operate the endoscopic instrument below the temperature range of 450°–500° C., heating element 12 may also be coated with an electrically-insulating "non-stick" coating. Such a coating reduces the accumulation of coagulum on the working surfaces of heating element 12 when operated at low temperatures. The application of such coatings to surgical instruments, including a description of preferred coatings for the present invention, are discussed in Shaw et al. U.S. Pat. No. 4,848,337, which is hereby incorporated by reference in it's entirety. This patent describes an abherent coating for reducing the adherence of tissue to a surgical instrument for incising and causing hemostasis. Such coating includes materials selected from the group consisting of silicones, polydimethyisiloxanes, fluoride-metal composites and fluorocarbon polymers.

If a non-stick coating is desired, the coating may, more preferably, be either a fluorine-containing mixture, such as polytetrafluoroethylene (PTFE), or a fluorotelomer-based mixture. In particular, the coating may be either of type XYLAN® 8110/870 Black, available from Whitford Corporation of West Chester, Pa., which is PTFE-based, or type VYDAX® 1000 FLUOROTELEMER DISPERSION, available from E. I. du Pont de Nemours & Co., Inc., of Wilmington, Del., which is a fluorotelomer based-mixture. VYDAX® is preferred for longer-lasting applications where the surgical instrument will be reused multiple times. Furthermore, the VYDAX® thickness should preferably be in the range of approximately 0.3 to 0.4 mil (0.0075 to 0.01 mm).

An important consideration for endoscopic "cutting" instruments is to reduce the exposure of non-operative tissue to surgically sharp edges. During manipulation of endoscopic instruments, inadvertent contacting of tissue might result in unwanted cutting (and associated bleeding). Hence, the endoscopic "cutting" instrument constructed in accordance with the present invention is "sharp" only when the cutting instrument is activated.

In accordance with the present invention, heating element 12 of FIGS. 1 and 2 may include a tapered edge 11, which is not surgically sharp at body temperature, but is able to cut tissue when heating element 12 is energized. A cross-sectional view of tapered edge 11 is shown in FIGS. 3A and 3B. This "thermally activated cutting" edge is accomplished by having heating element 12 heat the issue to weaken its structure. The weakened tissue may then be severed by a relatively blunt instrument compared to the mechanically sharp surgical edge required to sever tissue at body temperature. The preferred cutting edge of the present invention has a taper angle, theta, at the apex of heating element 12, in the range of approximately 15° to 50°, and more preferably, 20° to 40°. The cutting edge comprises material having hardness, as measured by the Rockwell Hardness Method, of less than about 40 Rockwell C. Such an edge, when heated to temperatures in excess of approximately 260° C., produces a precise incision through tissue, but is not hard enough to be ground with an edge sufficiently sharp to cut tissue at body temperature. Furthermore, instruments constructed in accordance with this feature of the present invention may be conveniently bent and configured during surgery, by the surgeon, to reach tissue regions not otherwise accessible.

Figure 4:
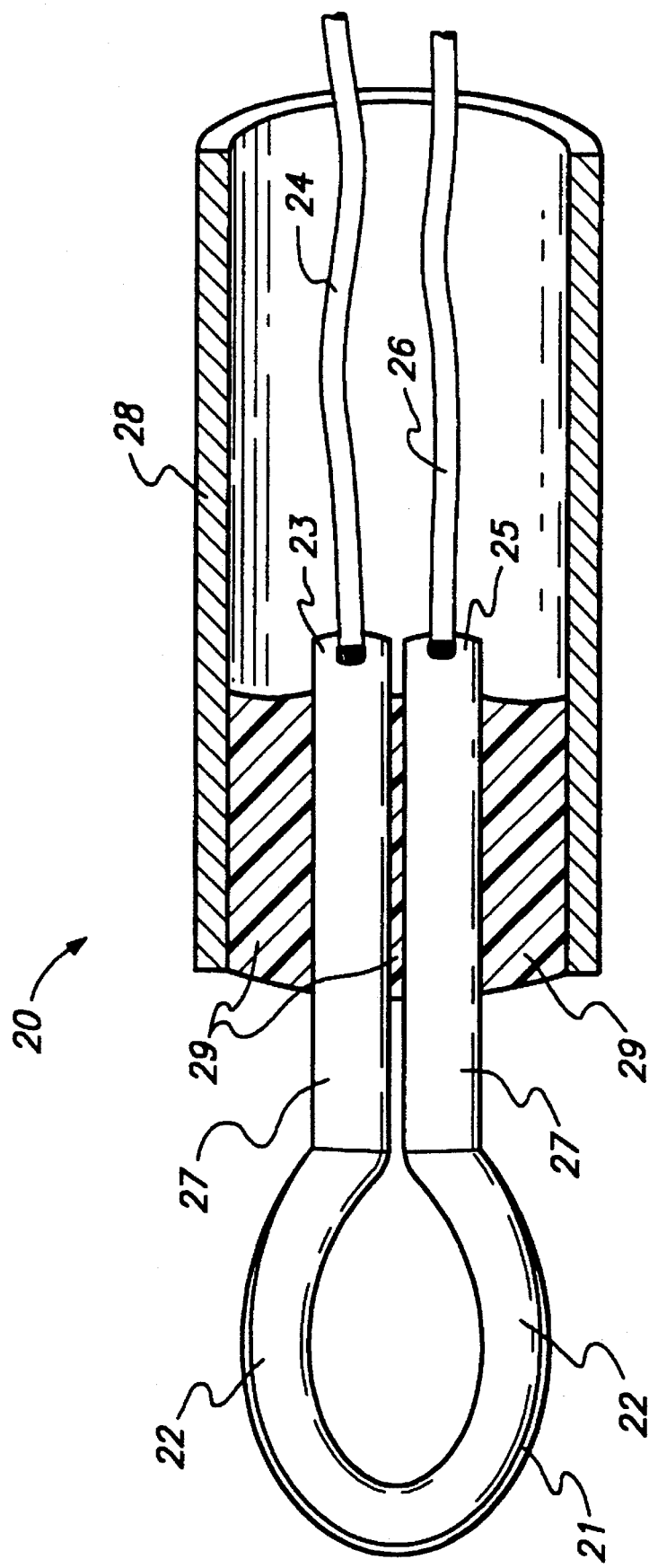
FIG. 4 is a cross-sectional view similar to FIG. 3, of an alternative dual-metal embodiment of the endoscopic instrument of the present invention.

Referring now to FIG. 4, an alternative embodiment 20 of the present invention is described. Endoscopic instrument 20 is similar in other respects to endoscopic instrument 10 shown in FIGS. 1–3, except for the addition of heater support member 27 interposed between heating element 22 and elongated shaft 28. Thus, endoscopic instrument 20 includes elongated shaft 28, electric leads 24 and 26, terminals 23 and 25, and potting material 29. The instrument may also include a tapered edge 21 for providing thermally-enhanced cutting.

Heater support member 27 is composed of a low thermal conductance material for limiting heat conduction from heater element 22 to the elongated shaft. Heater support member 27 reduces heating of the distal portion of elongated shaft 18, and thereby reduces the likelihood of heating tissue remote from the surgical site.

In accordance with the present invention, heater support member 27 furthermore does not itself generate heat due to the AC current that passes through it. As discussed above, it is desirable to confine and localize the high temperatures present in heating element 22 so as to not inadvertently damage or heat non-operative tissue. Thus, it is desirable to be able to maintain heater support member 27 and elongated shaft 28 at temperatures below approximately 60°–70° C. even when heater element 22 is at maximum operating temperature. Heater support member 27 has low thermal conductance and does not dissipate significant electrical power as current is conducted through it (i.e., has low electrical resistance). Thus, under these conditions, heater support member 27 stays at relatively low temperatures, compared to those experienced by heating element 22.

A preferred material for heater support member 27 comprises a low thermal conductivity nonferromagnetic metal or alloy such as stainless steel, for example, TYPE 304 stainless steel. The use of nonferromagetic alloys or metals in heater support member 27 allows the AC current passing to be conducted throughout substantially the entire cross section of the heater support.

Heater support member 27 may be connected to heater element 22 by any method that results in a low electrical resistivity junction. Such methods include thermally inert gas welding (TIG) and, more preferably, electron beam welding or laser-assisted welding.

Figure 5:
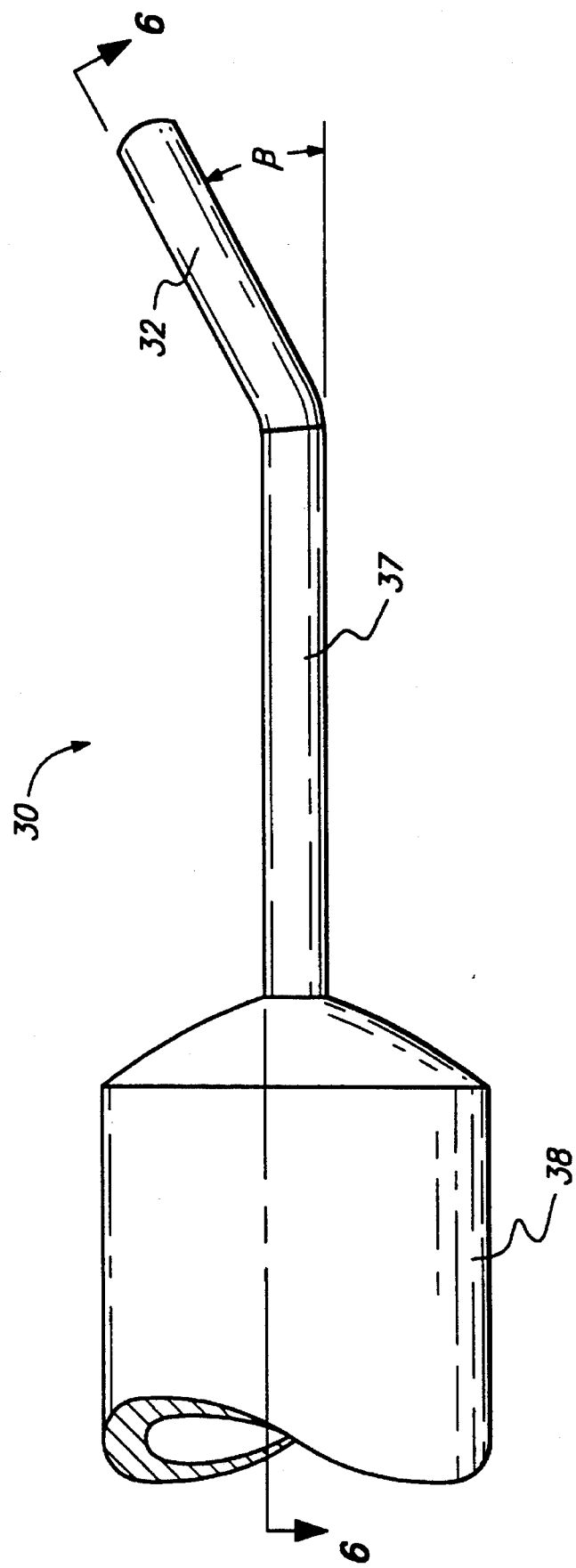
FIG. 5 is a side view a dual-metal endoscopic instrument of the present invention incorporating a serpentine-shaped heating element.
Figure 6:
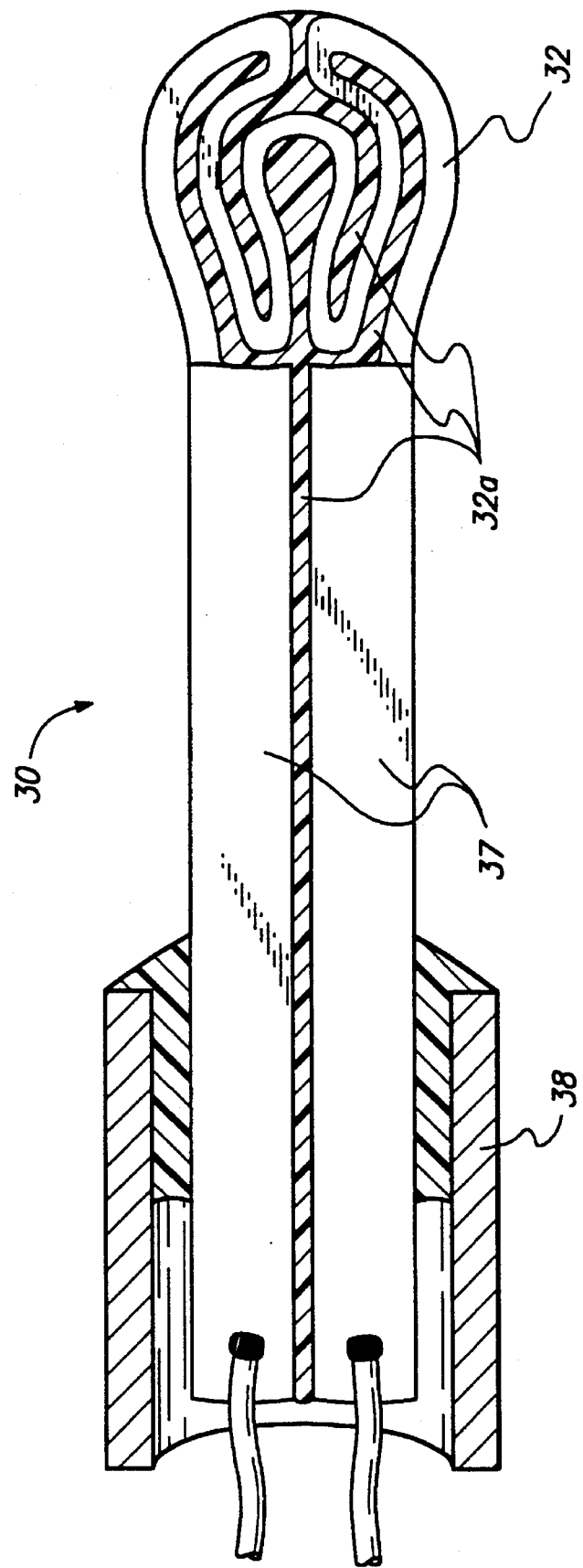
FIG. 6 is a plan view, partly in section, of the endoscopic instrument of FIG. 5, taken along line 6—6 of FIG. 5.

FIGS. 5 and 6 show a "serpentine" embodiment 30 of a heating element constructed in accordance with the present invention, wherein the "serpentine" heating element 32 is disposed at an angle beta to the longitudinal axis of elongated shaft 38. Angle beta is selected depending upon the type of endoscopic procedure to be employed, and may be, for example, 30 degrees. Heating element 32 is attached to elongated shaft 38 via low thermal conductance heater support member 37 that confines the heat generated in heating element 32 to the working surface. This embodiment provides an increased working surface area in comparison to the heating elements of FIGS. 1–4, as may be desirable for performing surgical procedures such as cauterization of tissues in the treatment of endometriosis. "Serpentine" heating element 32 may also include alumina cement 32a, or other similar material, to fill the air gaps between the scrolls of the heating element to provide a smooth, easy-to-clean surface.

As described hereinabove, the embodiments of the present invention of FIGS. 4–6, include a "heater support member" interposed between the heating element and the distal end of the elongated shaft. As discussed above, the heater support member reduces the leakage of heat from the heater element to the instrument shaft and is therefore fabricated from a material having a lower thermal conductance than the material comprising the heating element. Thus, the embodiments of FIGS. 4 to 6 may be referred to as "dual-metal" embodiments.

Figure 9A:
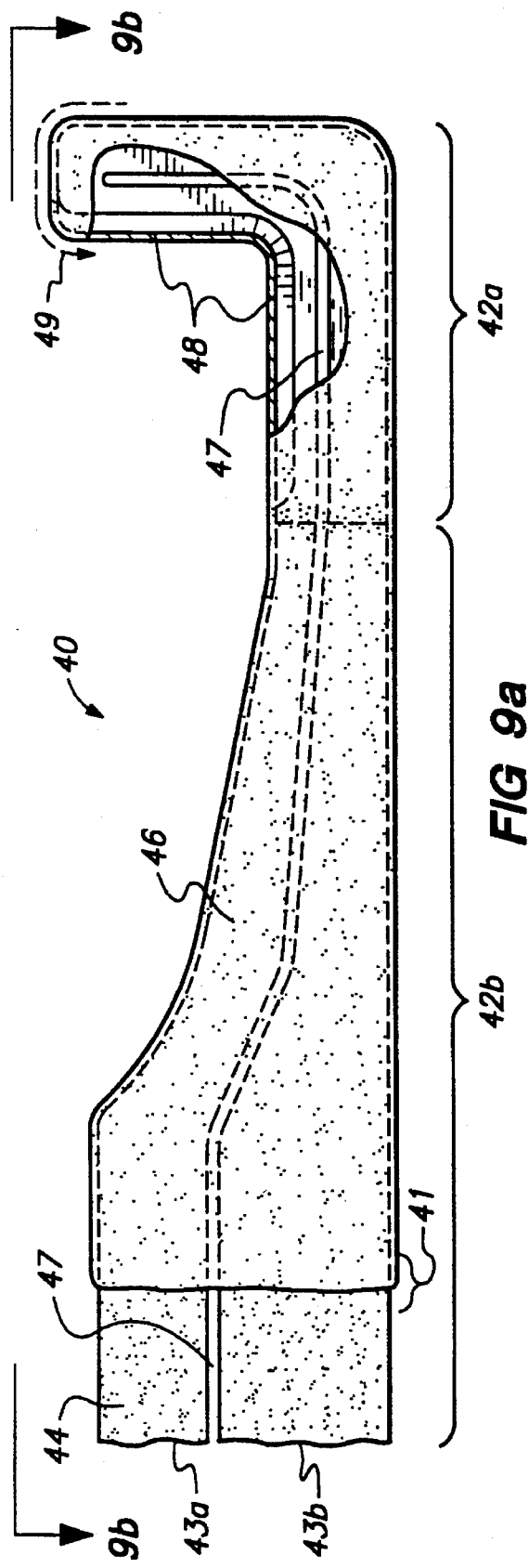
FIGS. 9A and 9B are, respectively, plan and elevation views of an endoscopic instrument similar to that of FIGS. 8A and 8B, further incorporating the optional non-stick coating of the present invention.
Figure 9B:
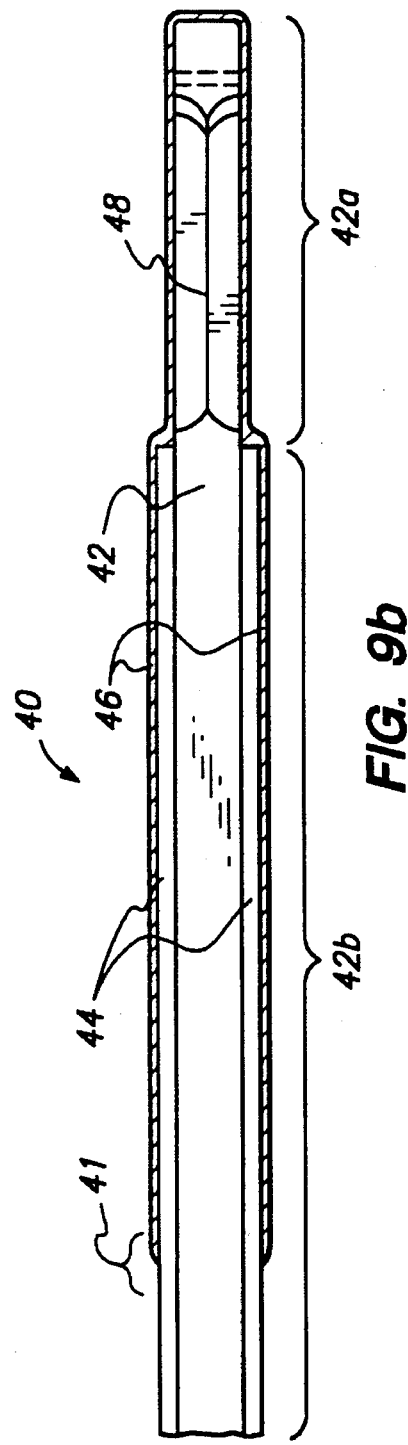

Referring now to FIGS. 7–9, preferred embodiments of monolithic heating elements of the present invention are described. Endoscopic heating element 40 of FIGS. 7A and 7B, includes auto-regulating metal substrate 42, overlayer 44, optional taper 48 (see FIGS. 8A and 8B) and optional non-stick coating 46 (see FIGS. 9A and 9B).

Auto-regulating metal substrate 42 comprises a ferromagnetic material, or other material which undergoes a similar transition in current conduction properties, when the temperature of the material varies. Suitable materials for use in heating element 40 are described hereinbefore with respect to the embodiments shown in FIGS. 1–6.

Auto-regulating metal substrate 42 has a high-temperature working surface region 42a and a low-temperature region 42b. An AC electric potential placed across terminals 43a and 43b in low-temperature region 42b causes an AC electric current to flow between terminals 43a and 43b and thus, through high-temperature working surface region 42a. Terminals 43a and 43b are separated by an isolation air gap 47, which electrically isolates terminal 43a from 43b, and which forces the AC current flowing through heating element 40 to conduct around loop 49 in high-temperature working surface region 42a. Isolation air gap 47, as was the case with the "serpentine" heating element shown in FIG. 6, may also be filled with alumina cement or other similar material to provide a smooth easy-to-clean surface. In accordance with the present invention, the AC current is conducted within the skin-depth of substrate 42 in high-temperature working surface region 42a and around loop 49. The resulting power dissipation heats region 42b to high temperatures sufficient to cause hemostasis of tissue and, if desired, thermally-enhanced cutting of the tissue (FIGS. 8A and 8B). Auto-regulation of the temperature of high-temperature working surface region 42a is achieved by constructing region 42a of auto-regulating metal, such as a ferromagnetic metal or the like, as discussed above with respect to the embodiments of the endoscopic instrument shown in FIGS. 1–6.

As for the previously-described embodiments, auto-regulating metal substrate 42 may be configured in a variety of shapes, depending upon the application of the particular endoscopic instrument. As described hereinbefore, substrate 42 may be constructed using a variety of methods and may include a thermally-enhanced cutting edge (FIGS. 8A and 8B).

Low-temperature region 42b of substrate 42 is covered with overlayer 44, a material that confines the heat generated in high-temperature working surface region 42a to the working surface area of the endoscopic instrument. Overlayer 44 may comprise a nonferromagnetic metal or alloy having a low thermal conductance and thus serves the same purpose as the heater support member discussed above with respect to dual-metal embodiments shown in FIGS. 4–6. However, in contrast to the embodiments of FIGS. 4–6, the low thermal conductance region is not separately welded or otherwise connected to the heating element 40. Thus, the embodiment of FIG. 7 comprises a monolithic heating element.

To reduce resistive heating of overlayer 44 caused by the AC current passing therethrough, the material comprising the overlayer should have a low electrical resistance in addition to low thermal conductance. Because of this preference for both low thermal conductance and low electrical resistance of overlayer 44, the selection of suitable materials for the overlayer may involve trade-offs with respect to the thickness, length and composition of the overlayer.

For example, since different metals and alloys have different values for both thermal conductivity and electrical resistivity, one metal may give low electrical resistance, but have high thermal conductance. Thermal conductance is proportional to the geometrical area and inversely proportional to the length of the thermal conductor, while electrical resistance has an opposite behavior (i.e., electrical resistance is inversely proportional to area and proportional to length). Thus, decreasing the thermal conductance of overlayer 44, by, for example, decreasing the cross-sectional area or increasing length of the overlayer metal, may have the opposite effect on electrical resistance (i.e., electrical resistance will increase).

Accordingly, the geometry and composition of overlayer metal will depend upon the particular working surface shape that is employed for the auto-regulating substrate metal, and the intended application of the resulting endoscopic instrument. For example, in applications where it is not critical to localize the high temperatures in the heating element, for a given geometry it may be desirable to select a material based on its resistivity, rather than its thermal conductivity. Conversely, it may be desirable to trade higher electrical resistance for lower thermal conductance in applications where it is more critical to be able to localize the high temperatures of the heating element.

It will be apparent to one skilled in the art that once the particular application for the endoscopic instrument has been decided, and the shape and heating requirements of the heating element have been established, the type and geometry of the particular overlayer metal can be determined. These parameters may be chosen either experimentally, for example, by measuring the localization of the heat (i.e., temperature as a function of distance along the endoscopic instrument), or by a combination of theoretical calculations and experimental measurements. Theoretical estimates may be obtained using conventional macroscopic steady-state equations for electrical resistance (i.e., Electrical Resistance=Resistivity×[Length/Area]) and thermal conductance (i.e., Thermal Conductance=Conductivity× [Area/Length]). Because the heating element is only heated for a few seconds at a time, the transfer of heat from the heating element to the low temperature region 42b may not reach steady-state, however, the use of these theoretical calculations, will for most cases provide adequate estimates of the performance characteristics of the heating element.

Preferably, the thickness of overlayer 44 should be thin enough so that electric current conducts throughout its entire cross-sectional area (i.e., the skin depth is many times its thickness) and thus the electric fields penetrate into the underlying auto-regulating metal substrate.

Overlayer 44 may comprise any metal or alloy that meets the desirable thermal conductance and electrical resistance characteristics requirements discussed above. Overlayer 44 may be disposed on auto-regulating metal substrate 42 using any technique capable of achieving a low electrical resistivity junction and intimate thermal contact with auto-regulating metal substrate 42, such as electroplating. Since plating thickness, produced by electroplating, is normally directly proportional to plating time, it may be advantageous to employ materials requiring thinner thicknesses to reduce the cost of the endoscopic instrument.

Metals fulfilling the above requirements include, among others, nickel and copper. For the particular embodiment of endoscopic instrument shown in FIGS. 7–9, and having auto-regulating substrate 42 comprising an 18-mil-thick alloy of iron and nickel, satisfactory performance has been obtained using overlayer 44 of electroplated copper, approximately 0.125 to 0.15 mil thick.

In FIGS. 8A and 8B, an alternative embodiment of a monolithic heating element similar to FIGS. 7A and 7B is described, in which an optional tapered edge 48 is incorporated into heating element 40 to provide thermally-enhanced cutting. Tapered edge 48 is constructed in accordance with the principles hereinbefore discussed with respect to the other embodiments of the heating elements shown in FIGS. 1–6.

Additionally, whether or not a tapered edge 48 has been incorporated into the endoscopic instrument, heating element 40 may also be provided with a non-stick coating 46 for reducing the accumulation of coagulum on the working surface, as shown in FIGS. 9A and 9B. Non-stick coating 46 is provided in accordance with the principles hereinbefore discussed with respect to the other embodiments of the heating elements shown in FIGS. 1–6. Additionally, in the preferred embodiment, non-stick coating 46 covers high-temperature working surface region 42a completely. Furthermore, if isolation air gap 47 is filled with an alumina cement or other similar material, the non-stick coating may also cover the cement to provide an easy-to-clean surface. As shown in FIGS. 9A and 9B, non-stick coating 46 covers only a portion of low-temperature region 42b (see transition region 41 in FIGS. 9A and 9B). Preferably, transition region 41 is placed inside the elongated shaft which heating element 40 would be disposed from. This reduces the exposure of non-coated material to tissue during surgery.

In the embodiments of the endoscopic instrument described above with reference to FIGS. 1–9, the heating element was shown to be "permanently" attached to the elongated shaft. In accordance with another feature of the present invention, there is provided an endoscopic instrument which includes a reusable universal handle which is capable of accommodating a wide variety of disposable working surfaces wherein a used working surface can be easily removed from the handle and replaced with a new or differently shaped working surface.

The above disposable working surface embodiment of the present invention eliminates the need to re-sterilize the working surface after each use—it is simply disposed of after use. Furthermore, it eliminates the need to employ a separate instrument for each type or configuration of working surface—one handle can accommodate a wide variety of working surfaces. It also allows a user to quickly interchange working surfaces during endoscopic surgery without the need to also change instrument handles or power supply connections. Thus, it can also save surgery time on the part of the user.

Figure 10A:
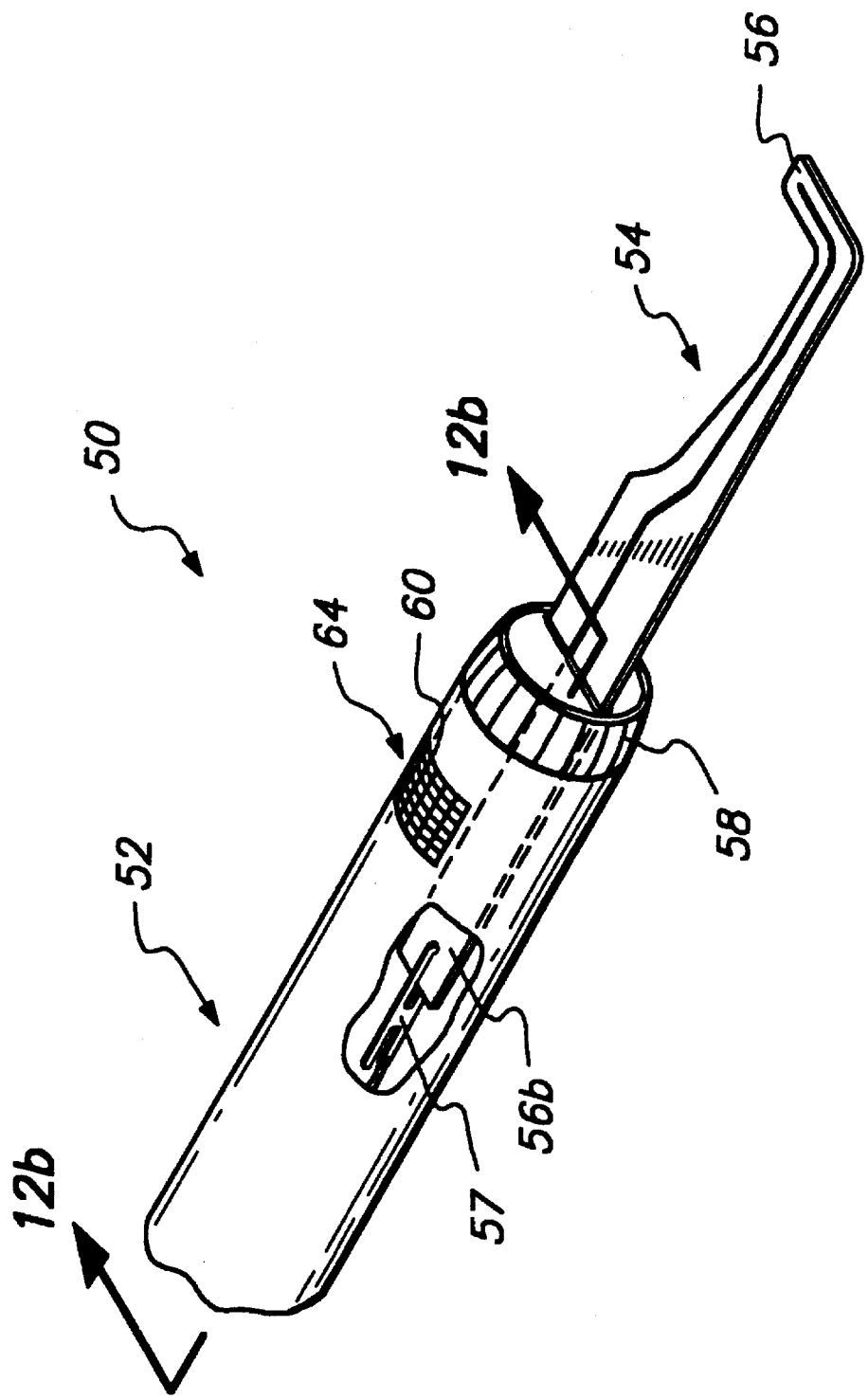
FIG. 10A is a perspective view of the distal end of an endoscopic surgical instrument having a disposable working surface constructed in accordance with the principles of the present invention.
Figure 10B:
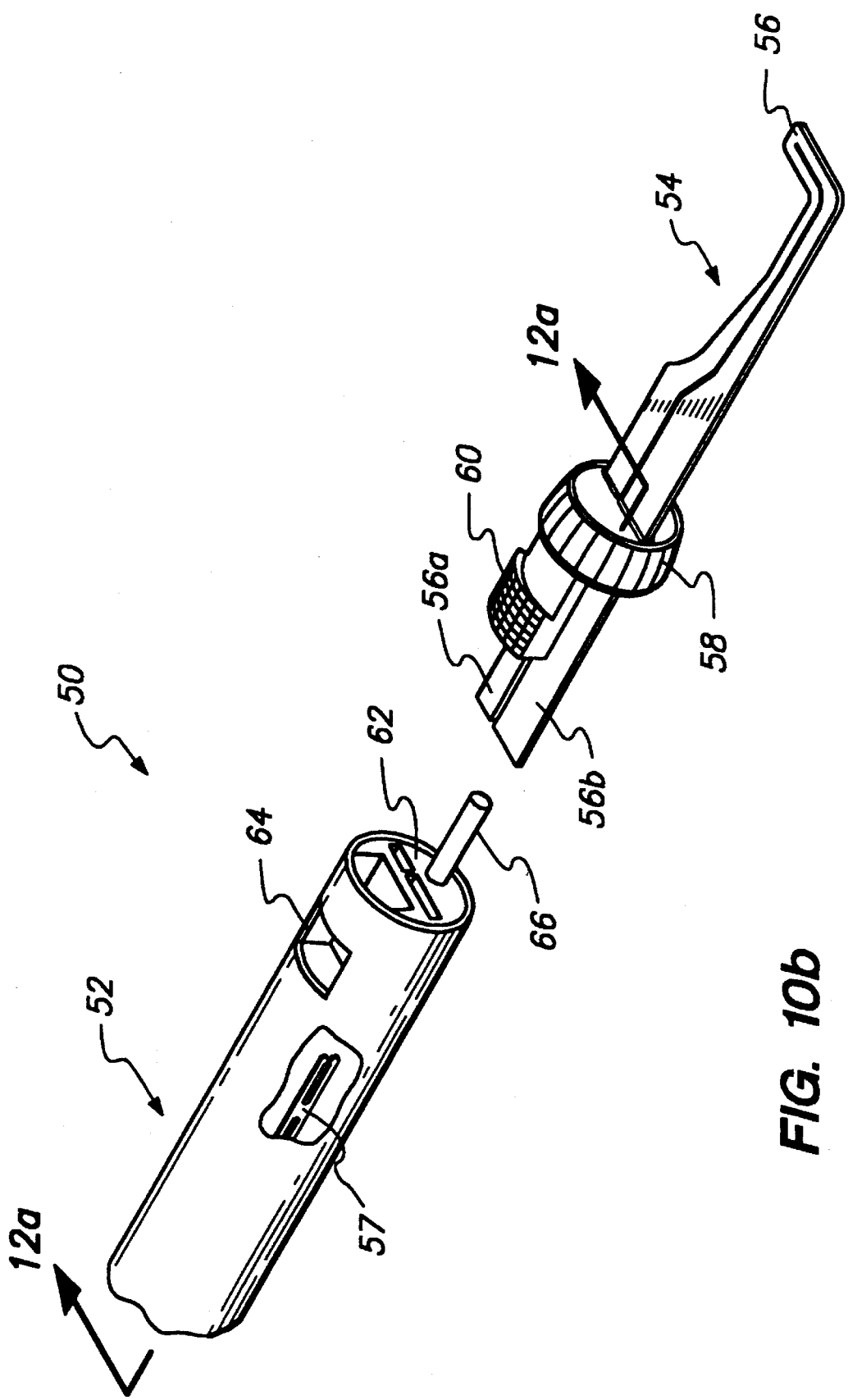
FIG. 10B is a perspective view of the distal end of the endoscopic surgical instrument of FIG. 10A prior to attachment of the disposable working surface to the instrument shaft.
Figure 11:
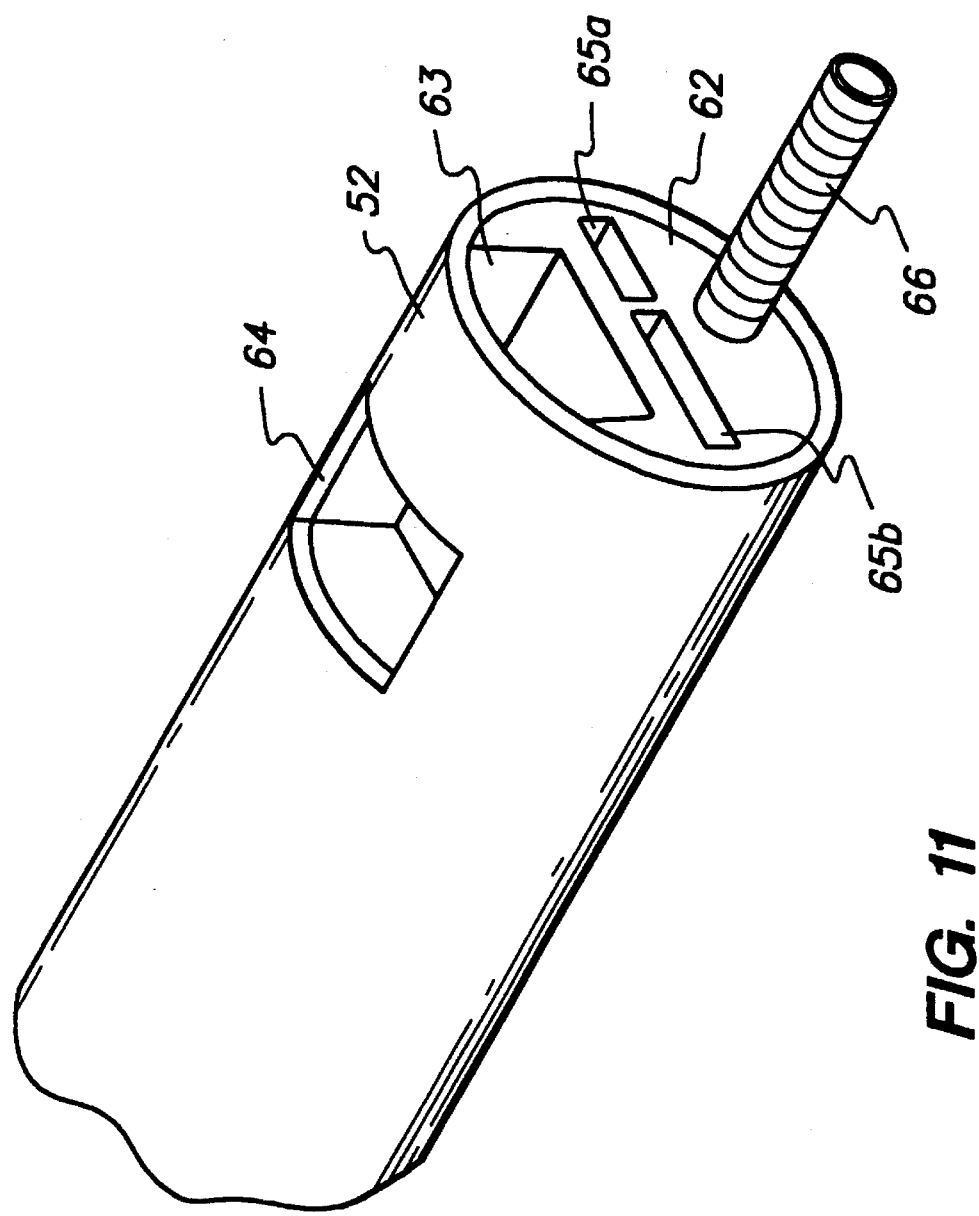
FIG. 11 is a detailed perspective view of the distal end of the reusable instrument shaft of FIG. 10B.

Referring the FIGS. 10–12, an illustrative embodiment of endoscopic instrument 50 including a disposable working surface is described. Endoscopic instrument 50 includes elongated shaft 52 and disposable working tip 54. Disposable working tip 54 is electrically energized as described hereinabove through heating element electrodes 56A and 56B.

As shown in FIGS. 10A, 10B and 11, disposable working tip 54 includes auto-regulating heating element 56 (similar to that described above with respect to FIGS. 8–9), end cap 58 and locking tongue 60. Elongated shaft 52 is designed to mate with disposable working tip 54. Accordingly, elongated shaft 52 includes receptacle 62 and locking window 64 which are adapted to provide a stable fit with disposable working tip 54. Receptacle 62 includes tongue insertion slot 63 (adapted to mate with locking tongue 60) and electrode insertion slots 65A and 65B (adapted to mate with heating element electrodes 56A and 56B, respectively).

Figure 12A:
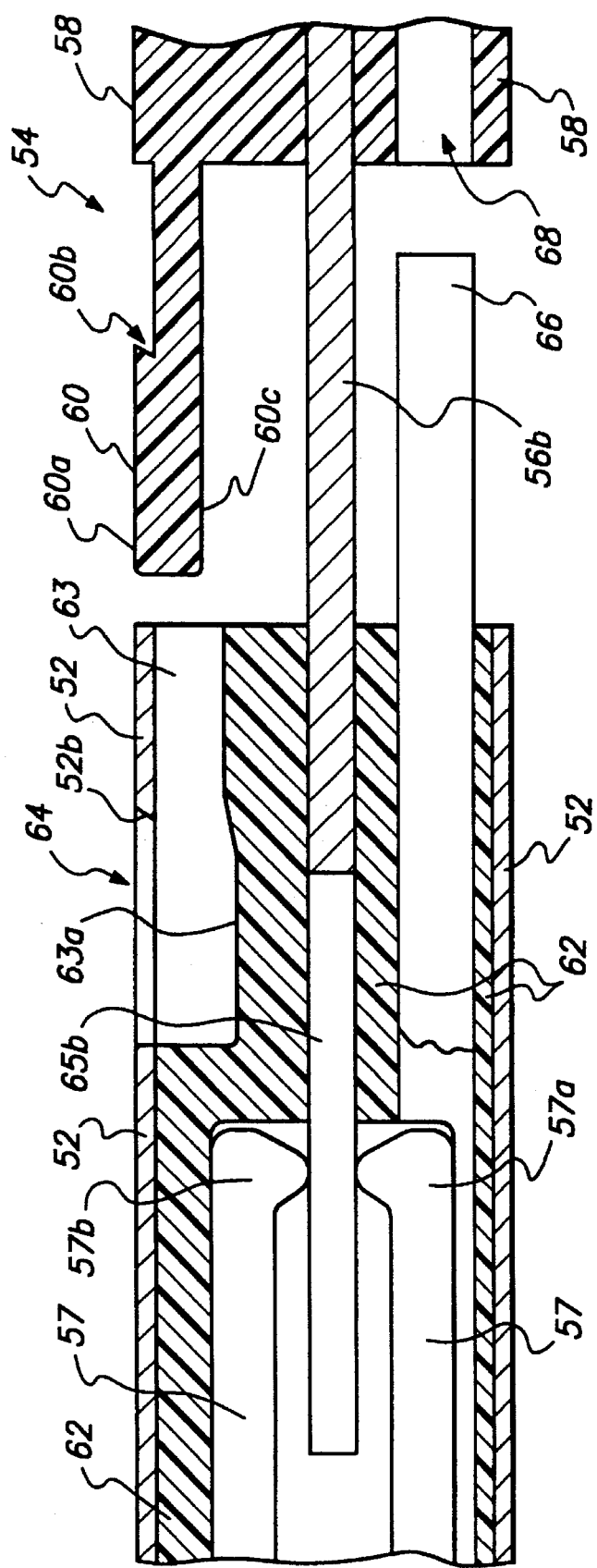
FIG. 12A is a cross-sectional view of the disposable endoscopic instrument of FIG. 10B, taken along line 12A—12A of FIG. 10B, during attachment of the disposable working surface to the instrument shaft.
Figure 12B:
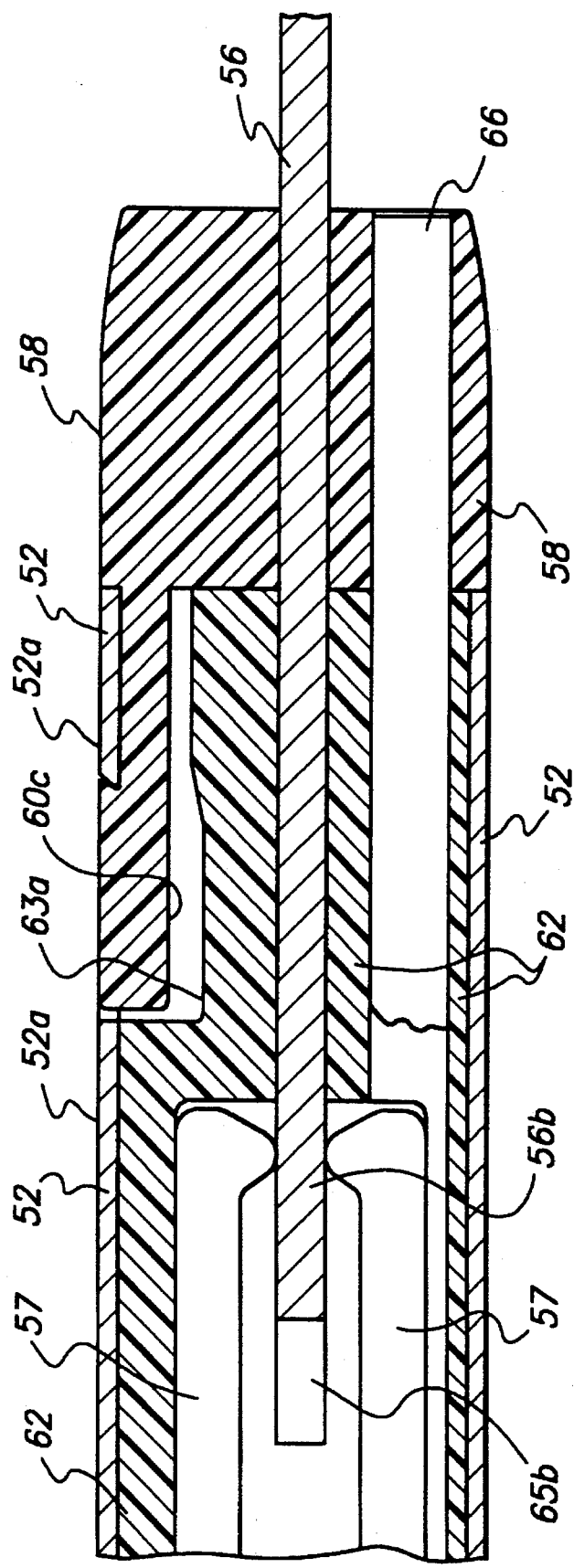
FIG. 12B is a cross-sectional view of the disposable endoscopic instrument of FIG. 10A, taken along line 12B—12B of FIG. 10A.

In accordance with the present embodiment, endoscopic instrument 50 includes optional tube 66 extending from receptacle 62 of elongated shaft 52. Tube 66 is intended to provide irrigation, or in the alternative, suction, during surgery. As shown in FIGS. 12A and 12B, tube 66 is adapted to fit into and through opening 68 in end cap 58 in order to facilitate irrigation or suction.

Tube 66 is preferably made from a material capable of withstanding the working temperatures experienced by heating element 56 and the conditions encountered during steam-sterilization procedures. Preferably, tube 66 is made from copper, brass, stainless steel or a high temperature plastic material. It will be apparent that irrigation or suction tube 66 could also be incorporated into any of the embodiments of endoscopic instruments discussed above with respect to FIGS. 1–9.

In addition to providing irrigation or suction during surgery, tube 66 facilitates the attachment of disposable working tip 54 to elongated shaft 52. Because tube 66 extends from receptacle 62 it allows a user to orient receptacle 62 with respect to working tip 54 without the need to particularly identify tongue insertion slot 63 prior to an attempt to insert locking tongue 60 into slot 63. This self-orienting feature fascilitates attachment of disposable working tip 54 onto elongated shaft 52.

For surgical applications where endoscopic instrument 50 does not need a tube for irrigation or suction, tube 66 may be replaced, if desired, with a solid stub or other equivalent extending member to facilitate the orienting of receptacle 62 with working tip 54, as discussed above.

As shown in FIGS. 12A and 12B, locking tongue 60 is designed so that it interengages with tongue insertion slot 63 and locking window 64. After insertion of disposable tip 54 into receptacle 62, radial-outward tension in locking tongue 60 causes surface 60A of locking tongue 60 to become substantially flush with outer surface 52A (FIG. 12B) of elongated shaft 52. Furthermore, locking tongue 60 includes an overhang edge 60B that is adapted to engage beveled edge 52B formed in the distal transverse edge of locking window 64. The above features associated with locking tongue 60 prevent unintentional detachment of disposable tip 54 from elongated shaft 52, especially during endoscopic surgery.

Disposable tip 54 is removed from elongated shaft 52 by depressing tongue 60 with one hand while simultaneously pulling tip 54 away from receptacle 62 with the other. Tongue insertion slot 63 includes a cavity 63A into which surface 60C flexes when locking tongue 60 is depressed for removal as can be seen in FIG. 12B.

In accordance with the present embodiment, end cap 58 and receptacle 62 are preferably made from a non-conducting injection moldable plastic capable of withstanding the temperatures produced by heating element 56 during operation. Furthermore, because receptacle 62 is permanently attached to elongated shaft 52 and not disposable as is end cap 58, receptacle 62 preferably should also be able to withstand conditions encountered during steam-sterilization procedures. More preferably, end cap 58 and receptacle 62 are made from polyetherimide or polysulfone materials.

Receptacle 62 and end cap 58 are preferably attached to elongated shaft 52 and heating element 56, respectively, using either locking pins (not shown) or adhesive. Of course, any other conventional attaching means may also be employed.

In accordance with the present invention, electrodes 56A and 56B are inserted, respectively, into electrode insertion slots 65A and 65B. When in locked and working position, electrodes 56A and 56B are electrically insulated from each other because receptacle 62 is made from a non-conducting material.

Figure 13A:
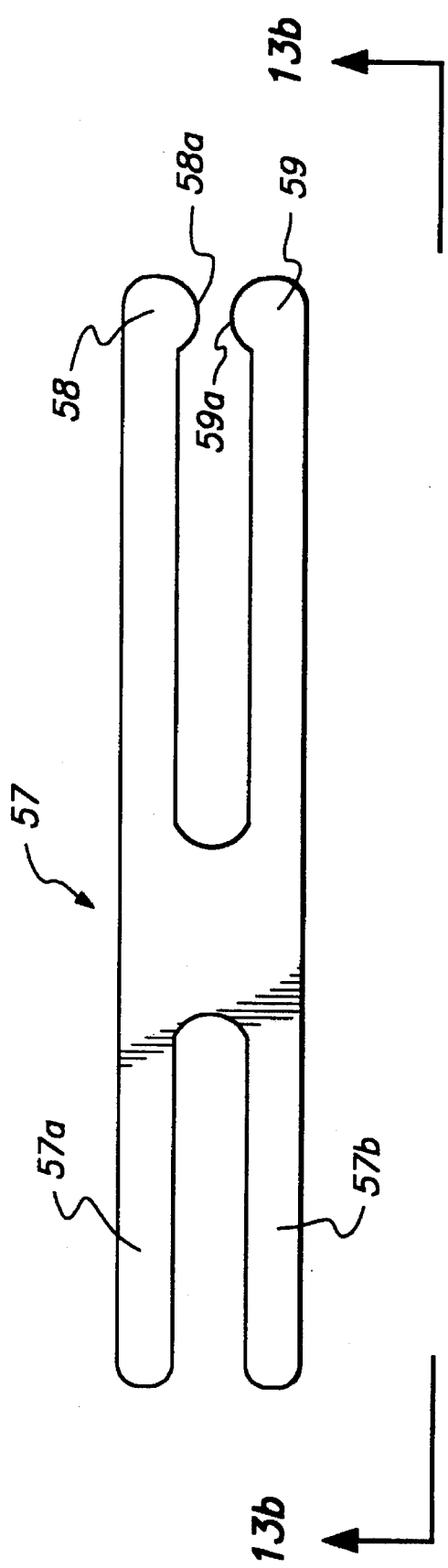
FIG. 13A is an elevation view of a preferred embodiment of an electrode contact made in accordance with the present invention.
Figure 13B:
FIG. 13B is a plan view of the electrode contact of FIG. 13A.

Electrode insertion slots 65A and 65B (FIGS. 12A and 12B) extend proximally inward along elongated shaft 52 to allow electrodes 56A and 56B to electrically connect to respective electrode contacts 57 (only one shown in figures). FIGS. 13A and 13B show a preferred embodiment of electrode contact 57 in isolation. Electrode contact 57 includes a pair of opposing contact fingers 58 and 59 having associated curved edges 58A and 59A, respectively. Curved edges 58A and 59A provide a tight mechanical and low resistance contact to electrodes 56A and 56B.

Electrode contact 57 includes a pair of electrode pins 57A and 57B on the opposite end from fingers 58 and 59. Electrode pins 57A and 57A are adapted to be inserted into an electrode contact receptacle (not shown) positioned inside elongated shaft 52. In the alternative, electrical connection to electrode contact 57 can be made by soldering wire thereto.

In order to provide the necessary spring force to facilitate a tight mechanical and low resistance contact to respective electrodes 56A and 56B, electrode contact 57 preferably should be made from a metal capable of repeatedly exerting adequate spring force (for example, an alloy of approximately 2% beryllium and 98% copper). In addition, it is preferable to coat or plate electrode contact 57 with a thin layer of gold (for example, 0.020 mil) to provide a low resistance electrical contact to electrodes 56A and 56B during repeated use. If desired, an intermediate layer of another metal can be used to assist in adhering the gold to the electrode metal (for example, 0.005 mil of nickel when the above beryllium-copper alloy is used).

If desired, the above-discussed non-stick coating could also be employed with the disposable working tip embodiment of the present invention.

Thus, it is seen that various embodiments of an instrument for endoscopic surgery have been provided. The instrument has a heating element with a working surface for providing hemostasis to tissue at an auto-regulated temperature. The working surface may also include a tapered edge for providing thermally-enhanced cutting of tissue, a non-stick coating for operating the instrument at low auto-regulation temperatures, or both. Processes for making such instruments have also been described.

In accordance with an additional aspect of the present invention, it is desirable that endoscopic instruments with auto-regulating heating elements are powered by a power source (see power source 9 in FIG. 1) that is capable of delivering a selectable and controlled amount of current to the heating element. The use of such selectable and controllable current, in combination with the auto-regulating heating element of the present invention, produces an endoscopic instrument with substantially stable temperature regulation, even after the activated heating element contacts colder tissue. In use, the high frequency current level is selected to elevate the heating element above it's auto-regulation temperature in the range of the Curie transition of the heating element. As the heating element contacts tissue and cools below the auto-regulation temperature, the skin depth decreases and, under constant current conditions, the amount of resistance heating increases.

A preferred power source capable of delivering a selectable and controllable current is described in commonly-assigned, co-pending U.S. patent application Ser. No. 07/877,454. This power supply is capable of delivering a substantially constant current level.

One skilled in the art will appreciate that the present invention can be practiced by other than the described embodiments, which are presented for purposes of illustration and not of limitation, and the present invention is limited only by the claims which follow.

What is claimed is:

1. A disposable working tip for use in endoscopically manipulating and coagulating tissue, the disposable working tip adapted to be removably connected to the end of a reusable elongated shaft, the disposable working tip comprising:

a working end having a working surface for contacting tissue and a cross-section extending perpendicularly to the working surface, the working end integrally formed of a heating element, the working surface maintained at an auto-regulated temperature by conducting a current throughout the entire cross-section of the working end, the heating element comprising a material having a skin depth extending substantially throughout the cross-section of said working end responsive to the temperature of the heating element and that decreases as the temperature of the heating element falls below the auto-regulated temperature;

first and second terminals electrically coupled to the working end and adapted to be removably coupled to the end of the reusable elongated shaft; and means for coupling the disposable working tip to the end of the reusable elongated shaft.

2. A disposable working tip as defined in claim 1 wherein the material further comprises a material that exhibits a Curie transition in permeability.

3. A disposable working tip as defined in claim 2 wherein the material further comprises a ferromagnetic material.

4. A disposable working tip as defined in claim 1 wherein the working surface further comprises a tapered edge for thermally-enhanced cutting of tissue at a temperature in the range of the auto-regulated temperature.

5. A disposable working tip as defined in claim 4 wherein the tapered edge defines an apex having an angle in the range of approximately 15 to approximately 50 degrees.

6. A disposable working tip as defined in claim 1 wherein the working end further comprises a material that can be bent and configured during surgery in order to reach tissue otherwise difficult to access.

7. A disposable working tip as defined in claim 1 wherein the working surface further comprises a coating of electrically-insulating non-stick material to reduce the accumulation of coagulum on the working surface.

8. A disposable working tip as defined in claim 1 further comprising:

an end cap having a passageway therethrough adapted to permanently hold the working end; and engagement means disposed on said end cap for removably attaching said disposable working tip to said end of the reusable elongated shaft.

9. A disposable working tip as defined in claim 8 wherein the reusable elongated shaft includes a portion defining a window and said engagement means includes a locking tongue adapted to interengage the window.

10. A disposable working tip as defined in claim 8 wherein said end cap includes a second passageway for allowing a tube to pass therethrough, said tube being permanently disposed from the end of the reusable elongated shaft.

11. A disposable working tip as defined in claim 10 wherein the tube is adapted to provide irrigation during surgery.

12. A disposable working tip as defined in claim 10 wherein the tube is adapted to provide suction during surgery.

13. An instrument for use in endoscopically manipulating and coagulating tissue comprising:

a reusable elongated shaft having a proximal end and a distal end, the proximal end having first and second electrical connectors adapted to be coupled to a power supply; and a working end having a working surface for contacting tissue and a cross-section extending perpendicularly to the working surface, the working end integrally formed of a heating element, the working surface maintained at an auto-regulated temperature by conducting a current throughout the entire cross-section of the working end, the heating element comprising a material having a skin depth extending substantially throughout the cross-section of the working end responsive to the temperature of the heating element and that decreases as the temperature of the heating element falls below the auto-regulated temperature;

first and second terminals electrically coupled to the working end and adapted to be coupled to the first and second electrical connectors, respectively; and means for removably coupling the working end to the distal end of the reusable elongated shaft.

14. An instrument as defined in claim 13 wherein the material further comprises a material that exhibits a Curie transition in permeability.

15. An instrument as defined in claim 14 wherein the material further comprises a ferromagnetic material.

16. An instrument as defined in claim 13 wherein the working surface further comprises a tapered edge for thermally-enhanced cutting of tissue at a temperature in the range of the auto-regulated temperature.

17. An instrument as defined in claim 13 wherein the working end further comprises a material that can be bent and configured during surgery in order to reach tissue otherwise difficult to access.

18. An instrument as defined in claim 13 wherein the working surface further comprises a coating of electrically-insulating non-stick material to reduce the accumulation of coagulum on the working surface.

19. A disposable working tip as defined in claim 13 further comprising:

an end cap having a passageway therethrough adapted to permanently hold the working end; and engagement means disposed on said end cap for removably attaching said disposable working tip to said end of the reusable elongated shaft.

20. An instrument as defined in claim 19 wherein the reusable elongated shaft includes a portion defining a window and said engagement means includes a locking tongue adapted to interengage the window.

21. An instrument as defined in claim 19 wherein said end cap includes a second passageway for allowing a tube to pass therebetween, said tube being permanently disposed from the distal end of the reusable elongated shaft.

22. An instrument as defined in claim 21 wherein the tube is adapted to provide irrigation or suction during surgery.

23. A disposable working tip for use in endoscopically manipulating and hemostatically cutting tissue, the disposable working tip adapted to be removably connected to the end of a reusable elongated shaft, the disposable working tip comprising:

a working end having a working surface for contacting tissue and a cross-section extending perpendicularly to the working surface, the working end integrally formed of a heating element, the working surface maintained at an auto-regulated temperature by conducting a current throughout the entire cross-section of the working end, the working surface including an atraumatic edge that becomes capable of cutting tissue when heated to a temperature in the range of the auto-regulated temperature, the heating element comprising a material having a skin depth extending substantially throughout the cross-section of said working end responsive to the temperature of the heating element and that decreases as the temperature of the heating element falls below the auto-regulated temperature;

first and second terminals electrically coupled to the working end and adapted to be removably attached to the end of the reusable elongated shaft; and means for coupling the disposable working tip to the end of the reusable elongated shaft.

24. A disposable working tip as defined in claim 23 wherein the material further comprises a material that exhibits a Curie transition in permeability.

25. A disposable working tip as defined in claim 24 wherein the material further comprises a ferromagnetic material.

26. A disposable working tip as defined in claim 23 wherein the atraumatic edge comprises a tapered edge defining an apex having an angle in the range of approximately 15 to approximately 50 degrees.

27. A disposable working tip as defined in claim 23 wherein the working end further comprises a material that can be bent and configured during surgery in order to reach tissue otherwise difficult to access.

28. A disposable working tip as defined in claim 23 wherein the working surface further comprises a coating of electrically-insulating non-stick material to reduce the accumulation of coagulum on the working surface.

29. A disposable working tip as defined in claim 23 further comprising:

an end cap having a passageway therethrough adapted to permanently hold the working end; and engagement means disposed on said end cap for removably attaching said disposable working tip to said end of the reusable elongated shaft.

30. A disposable working tip as defined in claim 29 wherein the reusable elongated shaft includes a portion defining a window and the engagement means includes a locking tongue adapted to interengage the window.

31. A disposable working tip as defined in claim 29 wherein said end cap includes a second passageway for allowing a tube to pass therethrough, the tube being permanently disposed from the end of the reusable elongated shaft, the tube adapted to provide suction or irrigation.

32. An instrument for use in endoscopically manipulating and hemostatically cutting tissue comprising:

a reusable elongated shaft having a proximal end and a distal end, the proximal end having first and second electrical connectors adapted to be coupled to a power supply; and a working end having a working surface for contacting tissue and a cross-section extending perpendicularly to the working surface, the working end integrally formed of a heating element, the working surface maintained at an auto-regulated temperature by conducting a current throughout the entire cross-section of the working end, the working surface including an atraumatic edge that becomes capable of cutting tissue when heated to a temperature in the range of the auto-regulated temperature, the heating element comprising a material having a skin depth extending substantially throughout the cross-section of the working end responsive to the temperature of the heating element and that decreases as the temperature of the heating element falls below the auto-regulated temperature;

first and second terminals electrically coupled to the working end and adapted to be coupled to the first and second electrical connectors, respectively; and means for removably coupling the working end to the distal end of the reusable elongated shaft.

33. A disposable working tip as defined in claim 32 wherein the material further comprises a material that exhibits a Curie transition in permeability.

34. A disposable working tip as defined in claim 33 wherein the material further comprises a ferromagnetic material.

35. A disposable working tip as defined in claim 32 wherein the atraumatic edge comprises a tapered edge defining an apex having an angle in the range of approximately 15 to approximately 50 degrees.

36. A disposable working tip as defined in claim 32 wherein the working end further comprises a material that can be bent and configured during surgery in order to reach tissue otherwise difficult to access.

37. A disposable working tip as defined in claim 32 wherein the working surface further comprises a coating of electrically-insulating non-stick material to reduce the accumulation of coagulum on the working surface.

38. A disposable working tip as defined in claim 32 further comprising:

an end cap having a passageway therethrough adapted to permanently hold the working end; and engagement means disposed on said end cap for removably attaching said disposable working tip to said end of the reusable elongated shaft.

39. A disposable working tip as defined in claim 38 wherein the reusable elongated shaft includes a portion defining a window and the engagement means includes a locking tongue adapted to interengage the window.

40. A disposable working tip as defined in claim 38 wherein said end cap includes a second passageway for allowing a tube to pass therethrough, the tube being permanently disposed from the end of the reusable elongated shaft, the tube adapted to provide suction or irrigation.

* * * * *